United States Patent [19]

Lonn

[11] Patent Number: 5,173,852
[45] Date of Patent: Dec. 22, 1992

[54] COMPUTED TOMOGRAPHY SYSTEM WITH TRANSLATABLE FOCAL SPOT

[75] Inventor: Albert H. R. Lonn, Wauwatosa, Wis.

[73] Assignee: General Electric Company, Milwaukee, Wis.

[21] Appl. No.: 540,995

[22] Filed: Jun. 20, 1990

[51] Int. Cl.⁵ .............................................. G06F 15/42
[52] U.S. Cl. ..................................... 364/413.14; 378/9
[58] Field of Search ................... 378/4, 8, 9, 10, 11, 378/19; 364/413.15–413.18, 413.14

[56] References Cited

U.S. PATENT DOCUMENTS

| | | | |
|---|---|---|---|
| 4,171,476 | 10/1979 | Waltham | 250/445 |
| 4,178,511 | 12/1979 | Hounsfield et al. | 250/445 |
| 4,412,289 | 10/1983 | Yamaguchi | 364/413.19 |
| 4,637,040 | 1/1987 | Sohval et al. | 378/9 |

OTHER PUBLICATIONS

"Reordering Schemes for Multiple-Rotation Fan-Beam CT Scanner", J. Jelinek and T. R. Overton, IEEE Transactions on Medical Imaging, vol. M1-4, No. 4, Dec. 1985.

*Primary Examiner*—Emanuel S. Kemeny
*Attorney, Agent, or Firm*—Quarles & Brady

[57] ABSTRACT

A CT apparatus for reducing aliasing in reconstructed images uses an x-ray tube with a translatable focal spot to double the spatial sampling rate, over that achieved by a conventional CT machine, by acquiring a first and second projection corresponding to two different focal spot positions. The amount of gantry rotation and the translation distance of the focal spot are coordinated so that the projections are interlaced and the resulting combined projection is geometrically indistinguishable from a conventional projection with twice the spatial sampling rate. The distance the focal spot is translated is further adjusted to eliminate redundant projections and provide adequate data acquisition time.

8 Claims, 5 Drawing Sheets

COMPUTED TOMOGRAPHY SYSTEM WITH TRANSLATABLE FOCAL SPOT

BACKGROUND OF THE INVENTION

This invention relates to computed tomography (CT) systems and specifically to a CT system having an x-ray tube whose focal spot may be controllably translated along the plane of the CT gantry rotation.

In a computed tomography system, an x-ray source is collimated to form a fan beam with a defined fan beam angle. The fan beam is oriented to lie within the x-y plane of a Cartesian coordinate system, termed the "imaging plane", and to be transmitted through an imaged object to an x-ray detector array oriented within the imaging plane. The detector array is comprised of detector elements, centered on a "pitch", each of which measure the intensity of transmitted radiation along a beam projected from the x-ray source to the particular detector element. The intensity of the transmitted radiation is dependent on the attenuation of the x-ray beam along that ray by the imaged object. The center of a beam and its intensity measurement may be identified to a ray described by the line joining the center spot of the x-ray source and the center of the detector element.

The x-ray source and detector array may be rotated on a gantry within the imaging plane and around the imaged object so that the angle at which the fan beam intersects the imaged object may be changed. At each gantry angle, a projection is acquired comprised of the intensity signals from each of detector elements. The gantry is then rotated to a new angle and the process is repeated to collect a number of projections along a number of gantry angles to form a tomographic projection set.

The acquired tomographic projection sets are typically stored in numerical form for computer processing to "reconstruct" a slice image according to reconstruction algorithms known in the art. A projection set of fan beam projections may be reconstructed directly into an image by means of fan beam reconstruction techniques, or the intensity data of the projections may be sorted into parallel beams and reconstructed according to parallel beam reconstruction techniques. The reconstructed tomographic images may be displayed on a conventional CRT tube or may be converted to a film record by means of a computer controlled camera.

The spatial resolution of the reconstructed CT image is dependant, in part, on the width of each x-ray beam at the center of the imaged object. This beam width is determined primarily by the source width, the size of the focal spot of the x-ray tube, and aperture of the detector element, and varies with distance from the source and detector. The averaging effect of a generally rectangular beam of width a, bandlimits the received image to a spatial frequencies of 1/a and less.

The beam spacing, defined near the center of the imaged object and determined by the detector pitch, controls the spatial sampling frequency of the CT system. Given the spatial bandlimit of 1/a, above, the sampling frequency must be approximately 2/a, per the Nyquist sampling thereon, to avoid aliasing effects in the reconstructed image. The elimination of aliasing therefore requires that the beam be sampled or read at distances separated by one half the beam width. Ordinarily, the beam width is optimized to be substantially equal to the beam spacing and therefore sampling is ideally performed no less than twice per beam spacing. This sampling will henceforth be referred to as double sampling.

A conceptually simple way to accomplish double sampling is to shift the detector elements one half of their pitch after a first sample and to take a second sample. In this way each beam is sampled twice in its width (and spacing). Nevertheless, the mechanical problems incident to rapidly and precisely moving the detector elements by one half their pitch (typically on the order of 1 mm) make this approach impractical. Rather, two other method are used:

The first method is to offset the detector elements in the plane of gantry rotation one quarter of the detector's pitch with respect to the gantry's axis of rotation. Beams projected through the imaged object at angles separated by 180° will be offset from each other by one half of the detector pitch and hence by one half the beam spacing for an optimized beam.

Although this method is relatively simple, it requires a full 360° of scanning and hence is not usable with reduced angle scanning techniques that acquire less than 360° of scanned data. Further, for this method to work properly, the imaged object must not move in between the acquisition of data for each offset beam. The length of time needed for the gantry to rotate 180° may be on the order of a second or more and hence motion of the imaged object is inevitable especially for organs such as the heart.

The second method of performing double sampling of each beam is to wobble the x-ray source by an amount that will shift each beam by one half its spacing. The wobbling is generally within the plane of rotation of the gantry and along the tangent to the gantry rotation. Wobbling of the x-ray source is easily accomplished electronically without mechanical motion of the x-ray tube. In an x-ray tube, an electron beam is accelerated against an anode at a focal spot to produce x-ray radiation emanating from the focal spot. The focal spot may be moved on the surface of the anode by the use of deflection coils or plates within the x-ray tube which deflect the electron beam either by the creation of a local magnetic or electrostatic field as is well understood in the art.

Double sampling may be performed by taking a first set of data with the x-ray spot in a first position on a first 360° scan; and taking a second set of data with the focal spot shifted to a second position on a second 360° scan. Preferably, however, to avoid motion problems between adjacent samples, the x-ray beam is rapidly shifted from one position to the other between each projection.

The rate at which the x-ray beam can be wobbled is limited by the acquisition time of the detector elements. This acquisition time, in turn, is dependant primarily on two factors: the decay time of the detector signal after stimulation by an x-ray beam and the desired signal-to-noise ratio of the projection data. The decay time is a function of the detector design. The signal-to-noise ratio is principally a function of the detector integration time, that is, how long the detector is allowed to collect x-ray energy.

The acquisition time restricts the rate at which the x-ray beam may be wobbled between focal spots to produce offset projections. Accordingly, and as will be explained in more detail below, the wobbled projections will be not only shifted by one half of the beam spacing with the movement of the focal spot of the x-ray tube (as desired) but also rotated from the ideal acquisition point by gantry rotation during the acquisition time. Therefore, one drawback to wobbling the x-ray source is that the projection data is not collected at the optimal positions for image reconstruction. Such misalignment between the data of a projection and its wobbled image degrades the resolution of the reconstructed image at points removed from its center.

SUMMARY OF THE INVENTION

The present invention relates to a method and apparatus for acquiring tomographic projection data that improves the spatial resolution of the data without the drawbacks previously associated with wobbling the focal spot. Specifically, a tomographic imaging system has an opposed x-ray source and plurality of periodically spaced x-ray detector elements mounted on a gantry which is rotatable about a center. The x-ray source is movable with respect to the gantry, either by deflecting the focal spot or some other method, generally within the plane of gantry rotation and along a tangent to the gantry rotation.

A first projection is acquired during which the gantry is rotated by an angle dT. The position of the x-ray source is then wobbled by an amount w and a second projection is acquired. The angle dT and distance w are chosen so that the second projection is interlaced with the first projection.

It is one object of the invention, therefore, to improve the spatial resolution of a CT projection without compromising the geometric integrity of the projection. By appropriately choosing the gantry rotation angle dT and the wobble distance w, the wobbled projection data may be aligned with the first projection data so that the combined first projection and wobbled projections are indistinguishable from a projection having decreased spacing between detectors and hence improved spatial resolution.

In one embodiment of the invention, the x-ray source is wobbled by an amount w that shifts the spatial location of the projection data by more than the pitch of the detectors. The gantry rotation dT is adjusted to preserve the interlacing of the first projection and the wobbled projection. This increased wobble w reduces the total number of projections produced by the wobbling of the x-ray source.

Thus, it is another object of the invention to increase the spatial resolution of the projection data without significantly increasing the number of projections that must be acquired and hence the amount of data that must be processed by the CT system.

Wobbling the x-ray source by an amount that shifts the spatial location of the projection data by more than the pitch of the detectors also increases the amount of gantry rotation necessary to interlace the two projection. This permits a longer integration time of the data for each projection.

It is thus another object of the invention to interlace the two projections formed by wobbling the x-ray source without substantially limiting the acquisition time of each projection. A longer acquisition time permits the use of slower detectors and improves the signal-to-noise ratio of the projection data.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DETAILED DESCRIPTION OF THE PREFERRED EMBODIMENT

Figure 1:
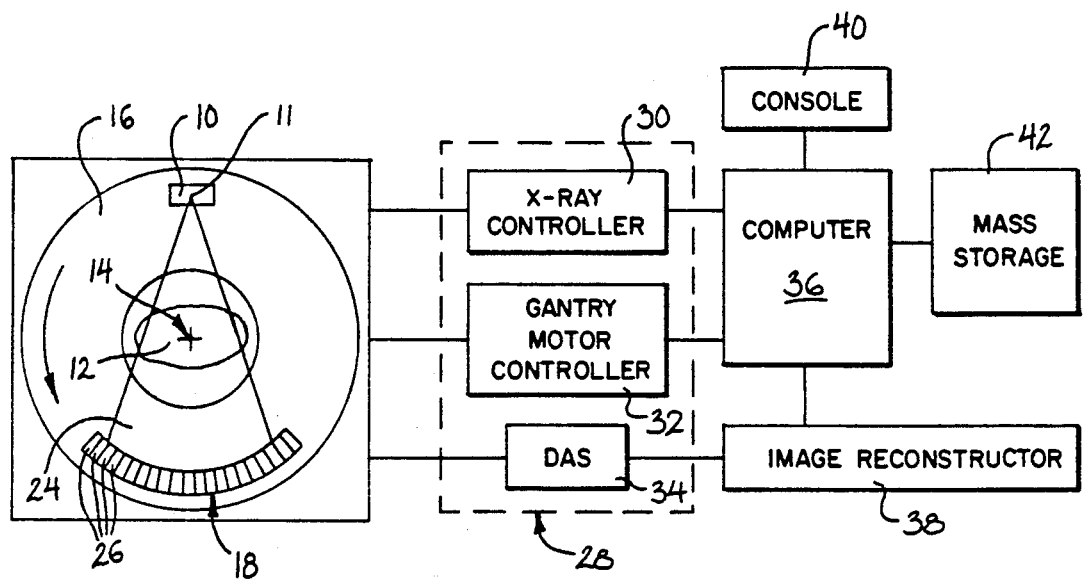
FIG. 1 is a schematic representation of a CT system suitable for use with the present invention.

Referring to FIG. 1, a CT gantry 16, representative of a "third generation" CT scanner includes an x-ray source 10 oriented to project a fan beam of x-rays 24 from a focal spot 11 through imaged object 12 to detector array 18. The detector array 18 is comprised of a number of detector elements 26 which together detect a projected image resulting from the transmission of x-rays through the imaged object 12. The gantry 16 rotates about a center of rotation 14 positioned within the imaged object 12.

The control system of a CT scanner, suitable for use with the present invention, has gantry associated control modules 28 which include: x-ray controller 30 which provides power and timing signals to the x-ray source 10 and which controls the focal spot 11 position within the x-ray tube, gantry motor controller 32 which controls the rotational speed and position of the gantry 16, and the data acquisition system 34 which receives projection data from the detector array 18 and converts the data to digital words for later computer processing.

The x-ray controller 30 and the gantry motor controller 32 are connected to a computer 36. The computer 36 is a general purpose minicomputer such as the Data General Eclipse MV/7800C and may be programmed to synchronize the gantry motion with the position of the x-ray beam per the present invention as will be described in detail below.

The data acquisition system 34 is connected to image reconstructor 38 which receives sampled and digitized signals from the detector array 18 via the data acquisition system 24 to perform high speed image reconstruction according to methods known in the art. The image reconstructor 38 may be an array processor such as is manufactured by Star Technologies of Virginia.

The computer 36 receives commands and scanning parameters via operator console 40 which is generally a CRT display and keyboard which allows an operator to enter parameters for the scan and to display the reconstructed image and other information from the computer 36. A mass storage device 42 provides a means for storing operating programs for the CT imaging system, as well as image data for future reference by the operator.

Figure 2:
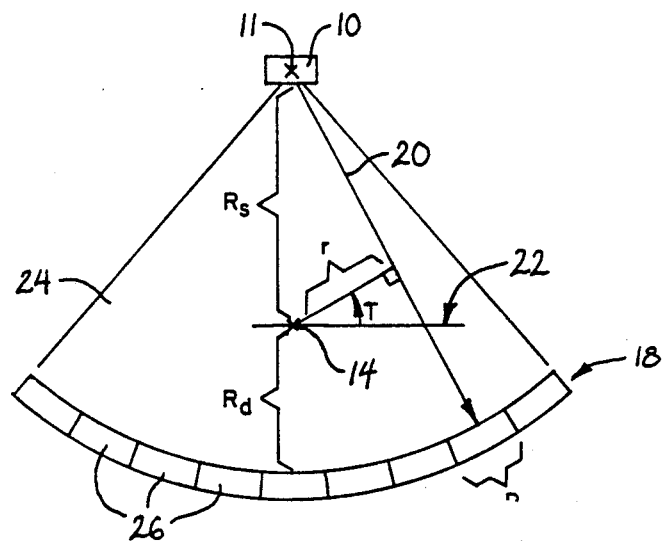
FIG. 2 is a detail of the fan beam of x-rays produced by the system of FIG. 1 showing the relative angles and axes associated therewith.

Referring to FIG. 2, the portion of the fan beam 24 associated with a particular detector element 26 may be identified by a ray 20 along a line through the center of the x-ray focal spot 11 and the center of the particular detector element 26. The ray 20 is in turn described by a radius line of perpendicular distance r from the center of rotation 14 to the ray 20 and an angle of rotation T of that radius from an arbitrary reference axis 22.

Figure 3:
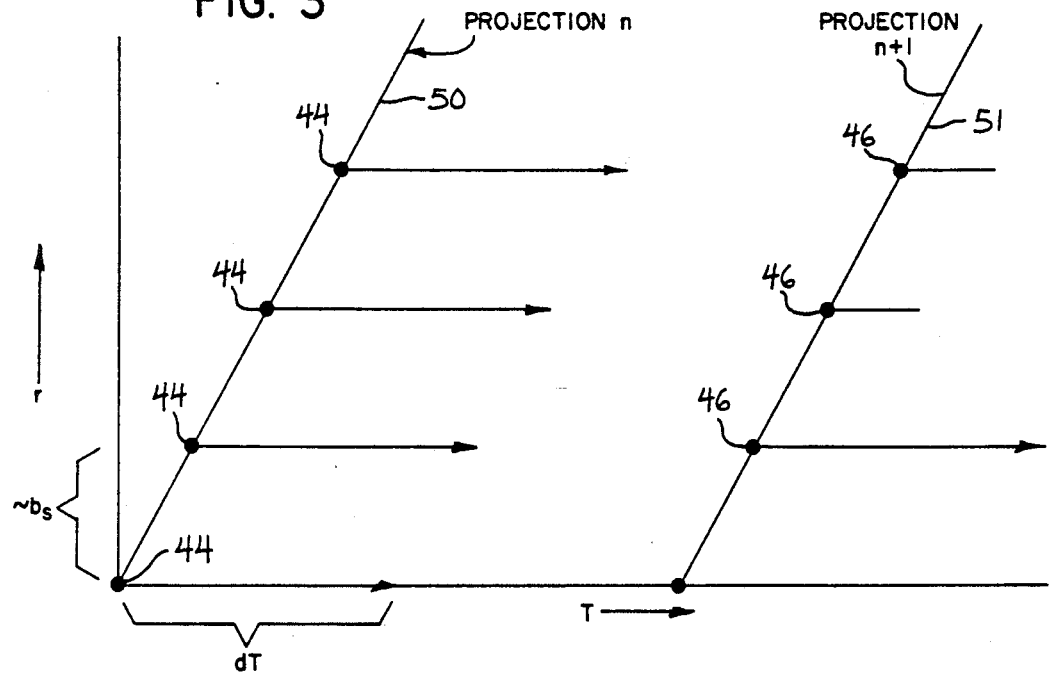
FIG. 3 is a plot of ray angle T and radius r of the projection data acquired with the CT system of FIG. 1 without wobbling the x-ray source.

The r and T value for each ray 20 may be mapped to an r-T diagram, such as is shown in FIG. 3, having horizontal axis of T and a vertical axis of r. At the start of the acquisition of the data for a projection n, the rays 20 of the projection are at the positions on the r-T diagram indicated by the closed circles 44. These closed circles 44 are along a projection line 50 defining the locus of points in the r-T diagram for a single projection. This projection line 50 is dependent on the geometry of the CT system and may be approximated as a straight line for the center rays 20 of the fan beam 24. For simplicity, the starting positions 44 of only three rays 20 are shown in FIG. 3, however, as is understood in the art, a projection normally includes nearly one thousand rays 20 and their corresponding intensity measurement data.

As the gantry 16 rotates, the positions of the rays 20 move horizontally along the r-T diagram from the closed circles 44. The horizontal lines correspond to increasing T caused by the gantry 16 rotation. The changing intensity of the x-ray radiation along the rays 20 is integrated by the detector elements 26 over angle dT indicated by the length of the horizontal lines on the r-T diagram and equal to the total gantry rotation for each projection. After the gantry 16 has rotated by dT, the projection is complete and no more data is taken until the gantry 16 has rotated to the starting location of the next projection n+1 indicated by projection line 50'. The starting positions for the rays 20 for this projection are indicated by closed circles 46.

Figure 4:
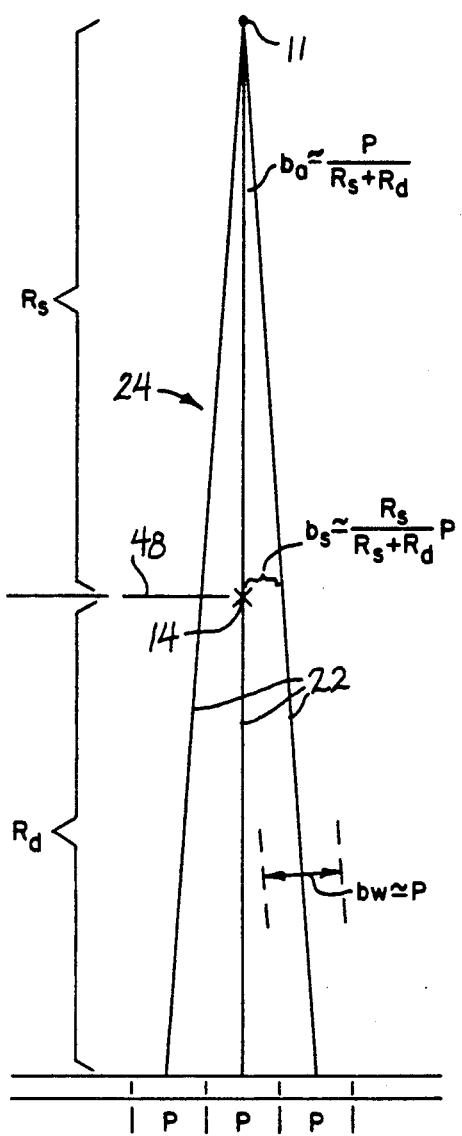
FIG. 4 is a detail of the fan beam of FIG. 2, showing the relationship between beam spacing, beam angle, and detector spacing.

The separation of the rays 20 along the r axis in r-T space determines the spatial sampling frequency of the projection data. As described above with regard to aliasing, this sampling frequency is approximated by the beam spacing which is fixed by the geometry of the detectors 18 and x-ray source 10. Referring to FIG. 4, the beam spacing $b_s$ is determined near the center of rotation 14 along line 48 perpendicular to the centermost ray 20 of the fan beam 24. The beam spacing ba is a function of the distance $R_s$ between the x-ray source 10 and center 14, the distance $R_d$ between the detectors 18 and center 14, and the pitch between detector elements P according to the following formula:

$$b_s = P \frac{R_s}{R_s + R_d} \quad (1)$$

This quantity is independent of the beam width $b_w$ which is determined by the size of the focal spot and the aperture of the detector elements 26. Nevertheless, the beam width is generally optimized to equal the beam spacing:

$$b_w \approx b_s \quad (2)$$

The beam width $b_w$ may be reduced further from the beam spacing $b_s$ by collimation, however the beam spacing $b_s$ for a single projection is fixed by the pitch of the detector elements 18.

As mentioned above, a second projection may be produced by wobbling the x-ray focal spot 11 and the spacing $b_s'$ between the beams of the first projection and the beams of the second projection may be varied arbitrarily depending on the amount the focal spot 11 is wobbled. This beam spacing $b_s'$ may be adjusted by the amount of the wobble w to provide a spatial sampling rate s times the beam width $b_s$.

The requirement for the elimination of aliasing as described above is that the sampling be at least twice for each beam width or $s \leq \frac{1}{2}$. As a result of the periodicity of the detector elements 18, however, the desired sampling rate may in fact be obtained with any odd integer multiple of this sampling rate or:

$$s = \left(N + \frac{1}{n}\right) \quad (3)$$

where n=2 for double sampling and

N=0,1,2,3 ...

If a projection is wobbled by one half its beam spacing, each ray forms a double sampled pair with the corresponding ray of the wobbled projection. If, however, a projection is wobbled by an amount greater than one half of its beam spacing, e.g. three halves, each beam forms a double sampled pair with the ray of the wobbled projection set corresponding to a neighbor.

Figure 5:
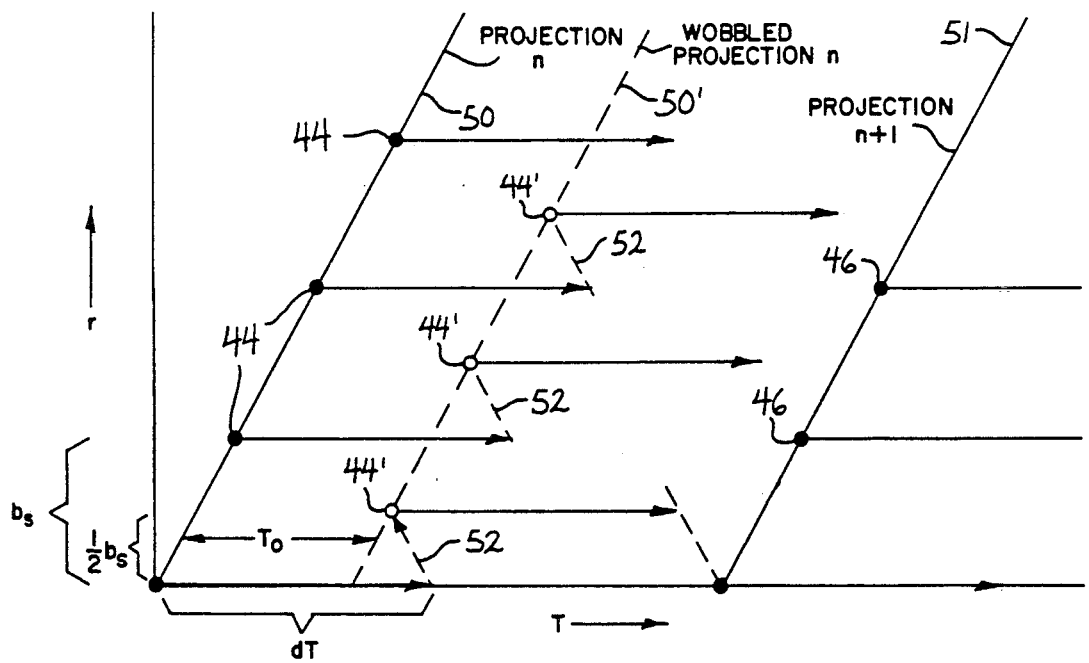
FIG. 5 is a plot of ray angle T and radius r similar to that of FIG. 3 but with wobbling of the x-ray source according to the background art.

Referring now to FIG. 5, in a projection n using spot wobbling, the rays 20 of the projection start at the positions indicated by the closed circles 44 along projection line 50. The signals from the detector elements 18 are integrated as the gantry 16 rotates through angle dT indicated by horizontal lines extending from the closed circles 44.

At the conclusion of this first projection n, the focal spot 11 is deflected to a new position. The effect of wobbling is to rapidly move the r and T position of the rays 20 along wobble trajectory 52 to the positions shown by the open circles 44' along wobble line 50. If the gantry 16 rotates in the direction of increasing T and the direction of wobble is opposite to the direction of gantry rotation, then the spot wobbles to a position 44' of lower T and higher r. The amount of movement of the focal spot 11 may be controlled so that the new position of the each ray 20 as shown by the open circles 44' is halfway between the positions 44. This provides the required double sampling needed to eliminate aliasing.

As mentioned before, the time taken by gantry rotation dT, before the focal spot 11 is wobbled, must be greater than or equal to a minimum amount dictated by data acquisition considerations. The required data acquisition time for the detectors 18 delays the starting positions 44' of the wobbled projection so that they are not aligned with the starting positions of the initial projection 44. Although the sampling shown in FIG. 5 is at half the beam spacing $b_s$, as required for double sampling, the starting positions of wobbled rays 44' have been shifted by $T_o$ from the first rays 44. This results from the fact that dT is chosen to divide the gantry rotation into the desired number of views independent of the amount of wobble.

Figure 6:
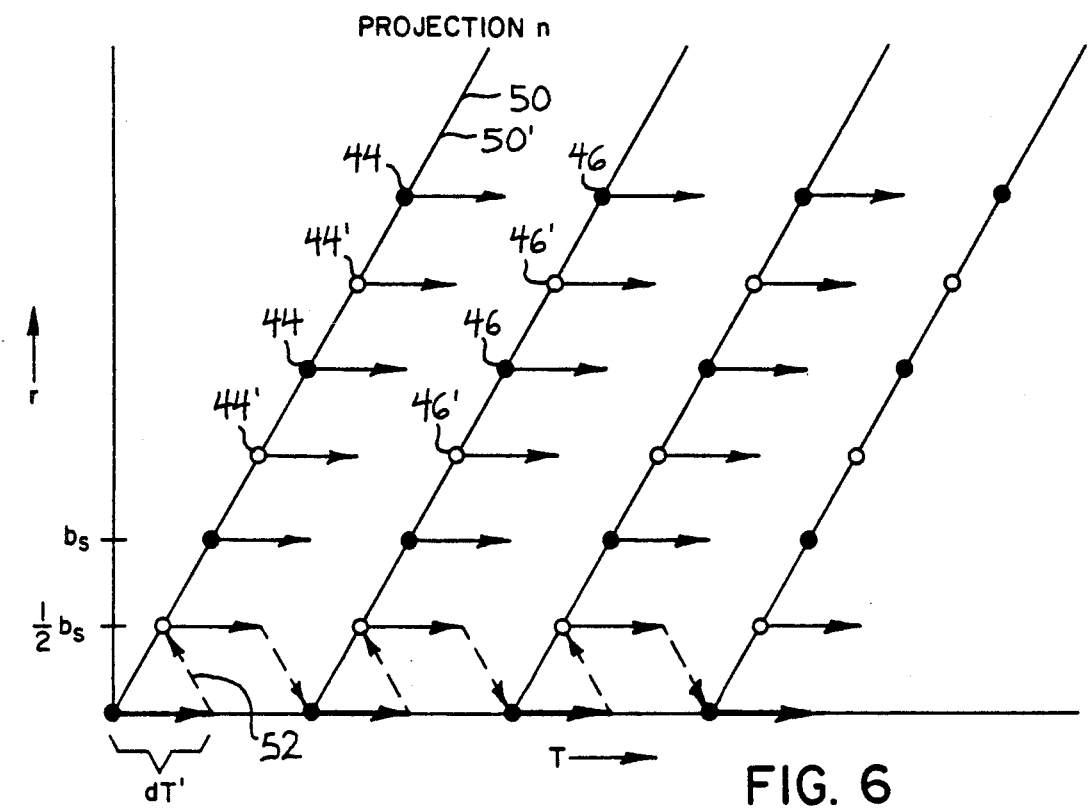
FIG. 6 is a plot similar to that of FIG. 5 but where the amount of wobble is coordinated with the angle of gantry rotation to interlace the two projections so created.

It is possible to align the data from the wobbled projection with the data of the earlier projection without wobble if there are no time limits imposed by the data acquisition on the rate of wobbling. Referring to FIG. 6, the amount of gantry rotation dT for a first projection n, before wobbling, can be limited to an amount dT' such that the projection line 50 of the starting positions 44 of the unwobbled projection is identical with the projection line 50' of the starting positions 44' of the wobbled projections. This condition of alignment will be termed "interlace".

The value of dT' needed for interlace may be determined as follows: Referring again to FIG. 4, for rays 20 near the fan beam's center the change in r between adjacent rays 20 will be approximately the beam spacing $$b_s = \frac{R_s}{R_s + R_d} \cdot P,$$

by equation (1) above. The change in T between such rays 20 will be approximately arctan $$\left(\frac{P}{R_d + R_s}\right)$$

or in this case because $P << R_s + R_d$ simply $$\frac{P}{R_d + R_s}.$$

The slope of the projection line 50 in r-T space will therefore be:

$$\frac{\frac{PR_s}{R_d + R_s}}{\frac{P}{R_d + R_s}} = R_s \qquad (4)$$

Figure 7:
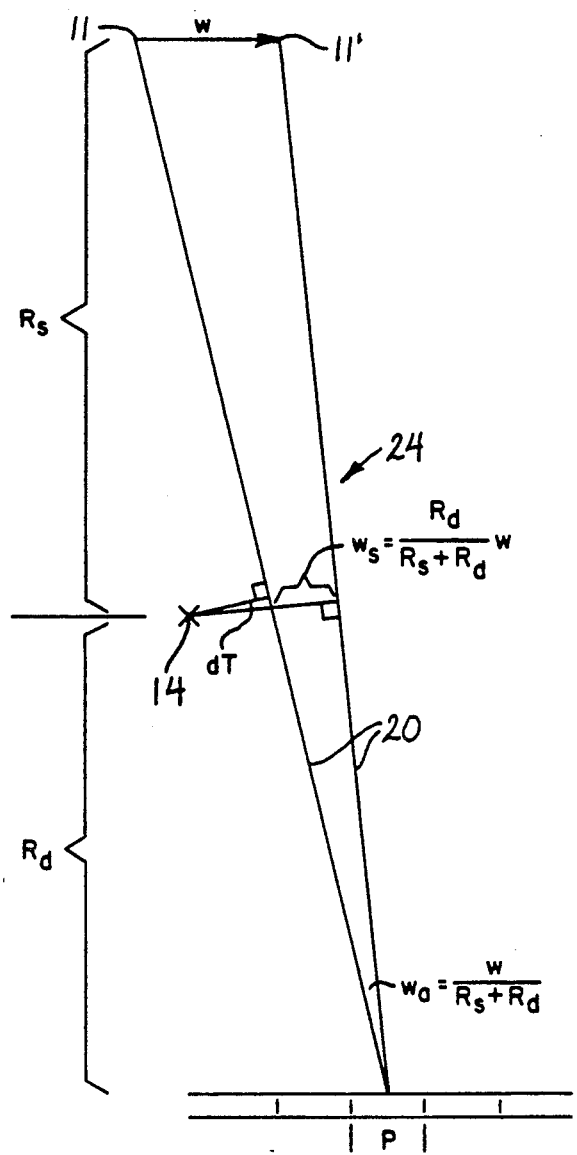
FIG. 7 is a detail of the fan beam of FIG. 2 showing the effect of wobbling the x-rays source on the geometry of the fan beam rays.

Similarly, referring to FIG. 7, for rays 20 near the center of the fan beam 24, a wobble of the focal spot 11 by a distance equal to w (where $w << R_s + R_d$) will change the r of a ray 20 by an amount equal to wobble spacing $$w_s = \frac{wR_d}{R_d + R_s}$$

and by an angle T equal to wobble angle $$w_a = -\frac{w}{R_d + R_s}.$$

The slope of the wobble trajectory 52 is therefore:

$$\frac{\frac{wR_d}{R_d + R_s}}{-\frac{w}{R_d + R_s}} = -R_d \qquad (5)$$

Figure 8:
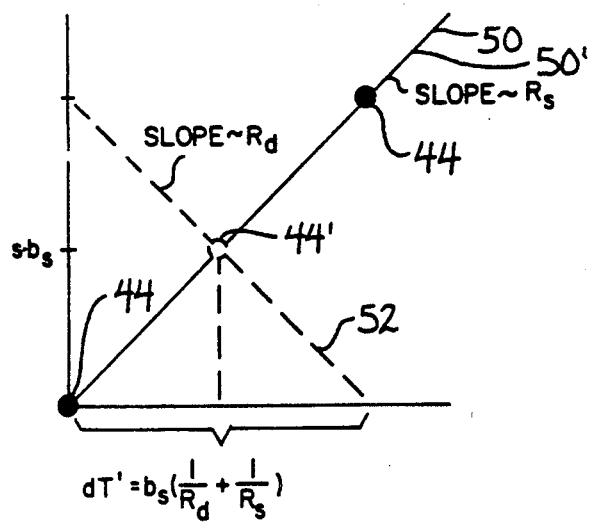
FIG. 8 is a detail of FIG. 6 showing the calculation of the relationship between gantry rotation dT and x-ray source displacement necessary to interlace the two projection sets produced by moving the x-ray source.

Referring now to FIG. 8, showing an enlarged portion of FIG. 6, the gantry rotation angle dT' necessary to interlace the projection lines 50 and 50' of the unwobbled and wobbled projections may be readily calculated from the slopes of the projection line 50 and wobble trajectory 52 and the desired sampling rate. Knowing that the wobble trajectory 52 and projection line 50 must intercept at the sampling distance $sb_s$ along the r axis from the previous line of unwobbled projection data, then:

$$dT = sb_s \left(\frac{1}{R_s} + \frac{1}{R_d}\right) \qquad (6)$$

or by substituting the value of $b_s$ given in equation (1):

$$dT = \frac{sP}{R_d} \qquad (7)$$

The required amount of wobble w of the focal spot 11 may be similarly determined. By equation for wobble shown in FIG. 7:

$$w = \frac{R_s + R_d}{R_d} \cdot w_s \qquad (8)$$

but $w_s = sb_s$ to provide the desired sampling so by equation (1):

$$w = sP\frac{R_s}{R_d} \qquad (9)$$

For the double sampling shown in FIG. 6, $s = \frac{1}{2}$, however the above equations hold true for any general sampling rate.

As mentioned, the rate of data acquisition shown in FIG. 6 may be too fast for the decay time of the detectors 18 or to fast to provide adequate integration time for acceptable signal-to-noise ratio in the data samples. Further, the total number of projections is markedly increased by such rapid wobbling resulting in unnecessary data and requiring additional data reduction steps.

Figure 9:
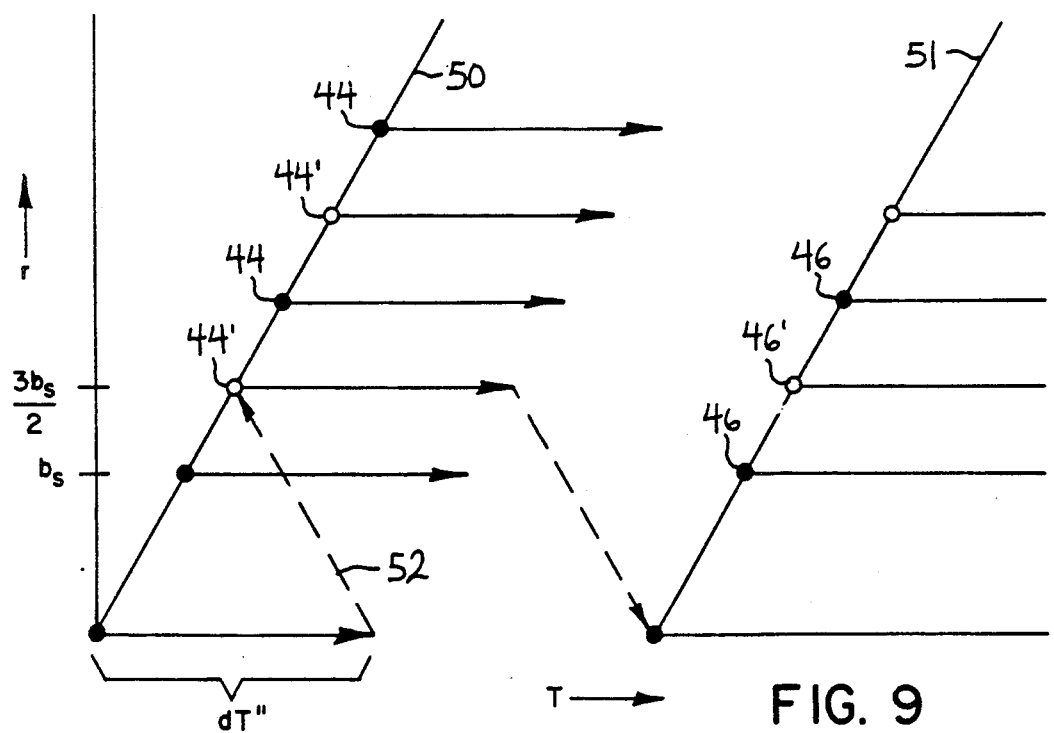
FIG. 9 is a plot similar to that of FIG. 6 but where the amount of wobble is greater than the detector pitch to decrease the number of projections and increase the acquisition time.

Therefore, in another embodiment of the invention, as shown in FIG. 9, the gantry rotation angle dT'' is much increased, as is the wobble distance w, so that wobbled projections 44 are interlaced with the unwobbled projections 44 wobbled by $$\frac{3b_s}{2}$$

rather than $$\frac{b_s}{2}$$

as shown in FIG. 6. The rotation of the gantry dT" required for this amount of increased wobble may be readily derived from the expression of equation (6) and is equal to $$dT = \frac{3b_s}{2}\left(\frac{1}{R_s} + \frac{1}{R_d}\right) \quad (10)$$

and the wobble amount w, by equation (9) is:

$$w = \frac{3b_s R_s}{2R_d} \quad (11)$$

In practice, the term N of the sampling rate s is chosen so as to produce the desired number of projections. For a given dT", the total number of projections will be equal to $$\frac{2\pi}{2dT''}.$$

Figure 10:
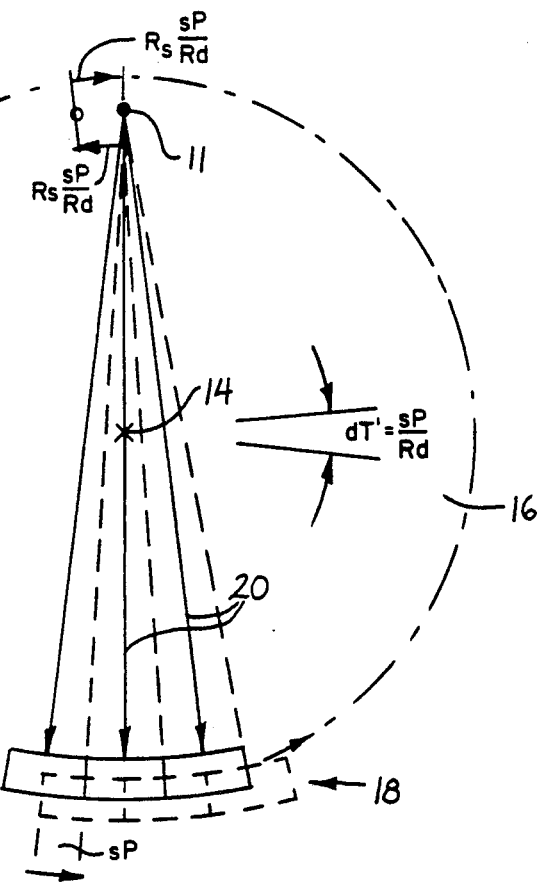
FIG. 10 is a detail of the fan beam of FIG. 2, showing the movement of the focal spot and the detector array for the amount of wobble of the present invention as depicted in FIG. 9.

The geometry of the movement of the focal spot 11 with respect to the detector array 18 for the condition of interlace may be understood by referring to FIG. 10. Per equation (7) above, the gantry 16 first rotates by an angle of $$dT = \frac{sP}{R_d}$$

so that each detector element 26 shifts by a distance $$R_d \frac{sP}{R_d} = sP$$

and the focal spot 11 shifts by a distance $$R_s \frac{sP}{R_d} = sP\frac{R_s}{R_d}.$$

Then the focal spot 11 is deflected by an exact amount $$w = sP\frac{R_s}{R_d}$$

per equation (9) equal to the above movement of the focal spot 11 caused by the gantry 16 rotation but in an opposite direction. Accordingly, the focal spot 11 returns to the same absolute position in space while the detectors elements 26 are shifted by sP, e.g., one half of their pitch if s°½.

Figure 11:
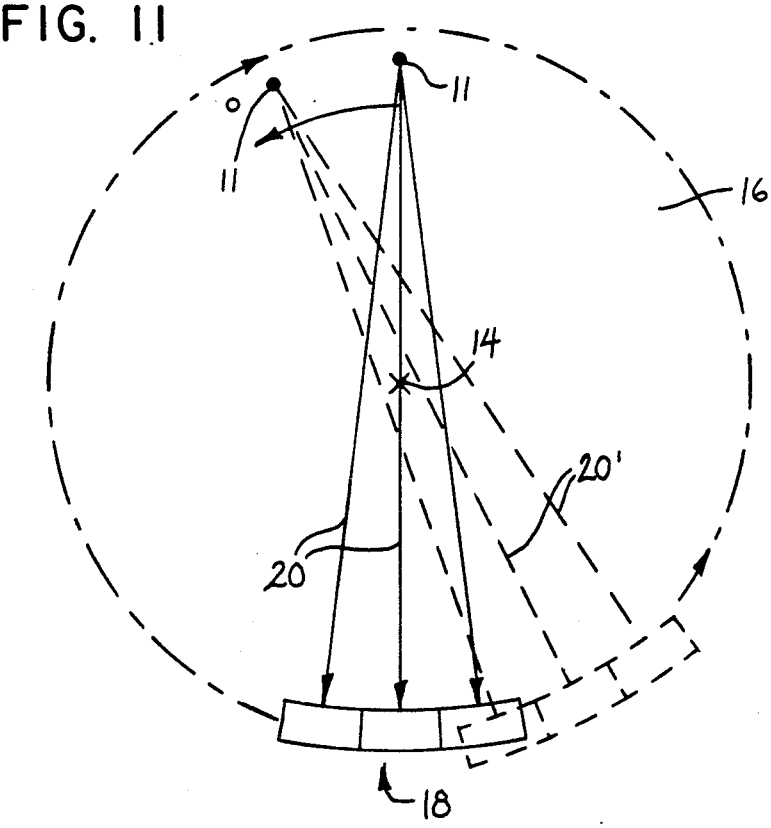
FIG. 11 is a detail of the fan beam of FIG. 2, showing the movement of the focal spot and the detector array for the amount of wobble of the background art as depicted in FIG. 5.

In distinction, the geometry of the movement of the focal spot 11 with respect to the detector array 18 for the "non-interlacing" method of FIG. 5, is depicted in FIG. 11. Here interlacing is not achieved because the focal spot 11 does not return to the same absolute position in space and hence the locus of points swept by the focal spot 11 during the subsequent gantry 16 rotation and integration period, shown also in FIG. 5, differs from the locus of points swept during the previous period of gantry rotation. It is noted that at points near the center of rotation 14 of the gantry 16, the shifting of the beams 20 by the rotation of the gantry 16 and the deflection of the focal spot 11 to create shifted beams 20' will be such as to correctly interspace the beams 20 and 20' for points near the center of the gantry rotation 14. However, because the shifted and unshifted beam 20 and 20' are not interleaved as defined herein, the correct spacing of the beams 20' is lost as the beams 20 and 20' converge to and diverge from the centerpoint 14.

Many modifications and variations of the preferred embodiment which will still be within the spirit and scope of the invention will be apparent to those with ordinary skill in the art. In order to apprise the public of the various embodiments that may fall within the scope of the invention, the following claims are made.

I claim

1. A method of acquiring projection data on a tomographic imaging system having opposed x-ray source and a plurality of periodically spaced x-ray detector elements mounted on a gantry rotatable at gantry angles about a center, said system usable for acquiring a series of projections of an imaged object each projection including projection data acquired along rays having angles T and radii r with respect to the center, the angles T and radii r forming a locus of points along a projection line, and where the x-ray source is movable with respect to the gantry generally within a plane of gantry rotation along a tangent to the gantry rotation comprising the steps of:

acquiring a first projection at a first gantry angle with the x-ray source in a first position with respect to the gantry and the rays of the projection having first values of T and r along the locus of a first projection line;

rotating the gantry by an angle dT during the first projection;

wobbling the x-ray source by a distance w to a second position with respect to the gantry; and acquiring a second projection, at a second gantry angle with the x-ray source in the second position with respect to the gantry wherein angle dT and distance w are chosen such that the rays of the second projection have second values of T and r along the locus of the first projection line.

2. The method of claim 1 wherein the angle dT equals $$\frac{sP}{R_d}$$

and the wobble distance w equals $$sP\frac{R_s}{R_d}$$

where:
P is the spacing between detector elements;
s is a desired spatial sampling frequency;
$R_s$ is the distance between the x-ray source and the center; and
$R_d$ is the distance between the detector and the center.

3. The method of claim 2 wherein s=½.
4. The method of claim 2 wherein s=3/2.
5. A CT apparatus for imaging a body comprising:
a gantry rotatable about a center;

an x-ray source mounted on said gantry for producing x-ray radiation from a first and second location with respect to the gantry and generally within the plane of rotation of the gantry and along a tangent to the gantry rotation;

a detector comprised of a plurality of periodically spaced detector elements having a separation distance P for measuring projection data from radiation received along rays from the x-ray source, sad rays having angle T and a radius r with respect to the center;

an x-ray control means for causing the x-rays from the x-ray source to shift between the two different locations to produce first and second projection data having first and second rays; and a gantry control means for coordinating the shifting of the x-ray source by the x-ray control means with the rotation of the gantry so that both the first rays and the second rays have values or r and T along a locus of a single projection line.

6. The apparatus of claim 5 wherein the gantry controller rotates the gantry by angle dT equal to $$\frac{sP}{R_d}$$

between the shifting of the x-rays from the first to the second location by wobble distance w equal to $$P\frac{R_s}{R_d}$$

where:
P is the spacing between detector elements;
s is the desired spatial sampling frequency;
$R_s$ is the distance between the x-ray source and the center; and
$R_d$ is the distance between the detector and the center.

7. The apparatus of claim 6 wherein $s=\frac{1}{2}$.
8. The apparatus of claim 6 wherein $s=3/2$.

* * * * *

UNITED STATES PATENT AND TRADEMARK OFFICE
CERTIFICATE OF CORRECTION

PATENT NO. : 5,173,852
DATED : December 22, 1992
INVENTOR(S) : Lonn

It is certified that error appears in the above-identified patent and that said Letters Patent is hereby corrected as shown below:

| | |
|---|---|
| Col. 5, line 68 | "ba" should be --$b_s$--. |
| Col. 8, line 26 | "dT" should be --dT'--. |
| Col. 8, line 33 | "dT" should be --dT'--. |
| Col. 9, line 11 | "dT" should be --dT'--. |
| Col. 9, line 25 | "2dT'" should be --2dT"--. |
| Col. 9, line 35 | "dT" should be --dT'--. |
| Col. 9, line 58 | "S°1/2 should be --S = 1/2--. |
| Col. 11, line 10 | "sad" should be -- said --. |

Signed and Sealed this

Second Day of November, 1993

Attest:

BRUCE LEHMAN

*Attesting Officer*   Commissioner of Patents and Trademarks